United States Patent
Zhang

(10) Patent No.: US 12,419,647 B2
(45) Date of Patent: Sep. 23, 2025

(54) LIGATION CLIP INCLUDING FLEXIBLE INSERT ASSEMBLY

(71) Applicant: Covidien LP, Mansfield, MA (US)

(72) Inventor: Zhihua Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 198 days.

(21) Appl. No.: 18/282,070

(22) PCT Filed: Mar. 16, 2021

(86) PCT No.: PCT/CN2021/081057
§ 371 (c)(1),
(2) Date: Sep. 14, 2023

(87) PCT Pub. No.: WO2022/193125
PCT Pub. Date: Sep. 22, 2022

(65) Prior Publication Data
US 2024/0148388 A1    May 9, 2024

(51) Int. Cl.
*A61B 17/122* (2006.01)
*A61B 17/00* (2006.01)

(52) U.S. Cl.
CPC .. *A61B 17/122* (2013.01); *A61B 2017/00004* (2013.01); *A61B 2017/00477* (2013.01); *A61B 2017/00858* (2013.01)

(58) Field of Classification Search
CPC ............ A61B 17/122; A61B 2017/122; A61B 17/1227; A61B 17/083; A61B 17/0487; A61B 17/08; A61B 2017/00584; A61B 5/6884
See application file for complete search history.

(56) References Cited

U.S. PATENT DOCUMENTS

| | | |
|---|---|---|
| 2001/0047164 A1 | 11/2001 | Teague et al. |
| 2008/0208324 A1 | 8/2008 | Glithero et al. |
| 2013/0240684 A1 | 9/2013 | Meyers et al. |
| 2014/0171986 A1 | 6/2014 | Shelton, IV |
| 2015/0040349 A1 | 2/2015 | Malia et al. |
| 2015/0164510 A1 | 6/2015 | Pleil et al. |
| 2018/0008447 A1* | 1/2018 | Jacobs ............ A61B 17/12099 |
| 2018/0036008 A1 | 2/2018 | Ramsey et al. |
| 2018/0146965 A1 | 5/2018 | Bachar |
| 2020/0008810 A1 | 1/2020 | Patel et al. |

FOREIGN PATENT DOCUMENTS

CN    106412182 A    2/2017
CN    110507381 A    11/2019

OTHER PUBLICATIONS

Extended European Search Report, EP 21930721, Dec. 4, 2024, 18pgs.
International Search Report and Written Opinion dated Dec. 14, 2021, issued in corresponding international application No. PCT/CN2021/081057, 11 pages.

* cited by examiner

*Primary Examiner* — Darwin P Erezo
*Assistant Examiner* — Zehra Jaffri
(74) *Attorney, Agent, or Firm* — Draft Masters IP, LLC

(57) ABSTRACT

A ligation clip(10) includes a hinge portion(300) having a flexible insert assembly(400) embedded in a body portion of the hinge portion(300). The flexible insert assembly(400) includes inserts(402, 404, 406) that are formed of a material that is more flexible than a material forming the body portion of the hinge portion(300). In this manner, plastic deformation in the hinge portion(300) of the ligation clip(10) is reduced or eliminated.

20 Claims, 4 Drawing Sheets

LIGATION CLIP INCLUDING FLEXIBLE INSERT ASSEMBLY

FIELD

The disclosure is generally related to surgical devices, and, more particularly, to a surgical ligation clip including a flexible insert assembly to reduce deformation in the surgical ligation clip.

BACKGROUND

Polymeric ligation clips typically include first and second beams that are coupled together at one end by a pivotable connection, e.g., living hinge, such that the first and second beams can be moved in relation to each other between open and clamped configurations. The ligation clips can be applied to tissue endoscopically through a small diameter incision or through a small diameter cannula positioned through the incision to minimize trauma to a patient during a surgical procedure.

Typically, when polymeric clips are applied to tissue through a cannula and/or stored within an endoscopic clip applier, the clips are supported in a compressed or partially compressed state to minimize an overall dimension of the clips and facilitate delivery of the clips through the cannula or incision. Storing polymeric clips in a compressed or partially compressed state may impact the condition of the clips which may impact the performance of the clips. More specifically, storing the polymeric clips in a compressed or partially compressed state causes strain and/or material creep in the material of the polymeric clip, especially in the region of the living hinge, which may adversely impact the condition and/or performance of the polymeric clip.

SUMMARY

In accordance with the disclosure, a ligation clip includes first and second arms and a hinge portion interconnecting the first and second arms. The first arm includes a first clamping surface and a first latching structure. The second arm includes a second clamping surface and a second latching structure. The hinge portion defines a bore and includes a body portion and a flexible insert assembly having first, second, and third inserts. The first and second arms are transitionable between an open configuration, in which, the first and second arms are spaced apart, and a clamped configuration, in which, the first and second latching structures of the first and second arms engage each other to clamp tissue between the first and second clamping surfaces. The first and second arms have a first rigidity. The body portion of the hinge portion has a second rigidity less than the first rigidity. One of the first, second, or third inserts of the flexible insert assembly of the hinge portion has a third rigidity less than the second rigidity.

In an aspect, the bore of the hinge portion may have a crescent shape when the first and second arms are in the open configuration.

In another aspect, the second and third flexible inserts of the flexible insert assembly may be disposed adjacent respective ends of the bore of the hinge portion.

In yet another aspect, the first insert of the flexible insert assembly may partially define the bore of the hinge portion.

In still yet another aspect, the first insert may include an anchor portion configured to inhibit movement of the first insert relative to the body portion of the hinge portion.

In an aspect, the anchor portion may have a shape of an arrow.

In another aspect, the first or second latching structure may be a hook.

In yet another aspect, the rigidity of the first insert may be different from the rigidities of the second or third insert.

In yet another aspect, the rigidities of the second and third inserts of the flexible insert assembly may be different.

In still yet another aspect, the first, second, or third inserts may be formed of a polymer.

In an aspect, the ligation clip may be formed of an absorbable polymer.

In another aspect, at least one of the second or third inserts may have a semi-circular shape.

In yet another aspect, the first or second clamping surfaces may include teeth to grip tissue.

In accordance with another aspect of the disclosure, a ligation clip includes first and second arms and a hinge portion interconnecting the first and second arms. The first and second arms includes first and second clamping surfaces, respectively. The first arm is movable in relation to the second arm to move the ligation clip from an open configuration, in which, the first and second clamping surfaces are spaced apart, to a clamped configuration, in which, at least portions of the first and second arms engage each other to clamp tissue between the first and second clamping surfaces. The hinge portion includes a body portion and flexible inserts embedded in the body portion. The flexible inserts have a rigidity less than a rigidity of the body portion. The flexible inserts are peripherally arranged about the hinge portion and spaced apart from each other.

In an aspect, the first and second arms may include respective latch portions engaging each other when the ligation clip is in the clamped configuration to retain the first and second arms in the clamped configuration.

In another aspect, the flexible inserts may include a pair of semi-circular inserts.

In yet another aspect, the hinge portion may define a bore.

In yet another aspect, the bore of the hinge portion may have a crescent shape when the ligation clip is in the open configuration.

In still yet another aspect, the flexible inserts may include a central insert disposed adjacent the bore.

In still yet another aspect, the central insert may include an anchor portion configured to inhibit movement of the central insert relative to the body portion of the hinge portion.

BRIEF DESCRIPTION OF THE DRAWINGS

Various aspects of the ligation clip are described herein below with reference to the drawings, wherein.

DETAILED DESCRIPTION

Figure 1:
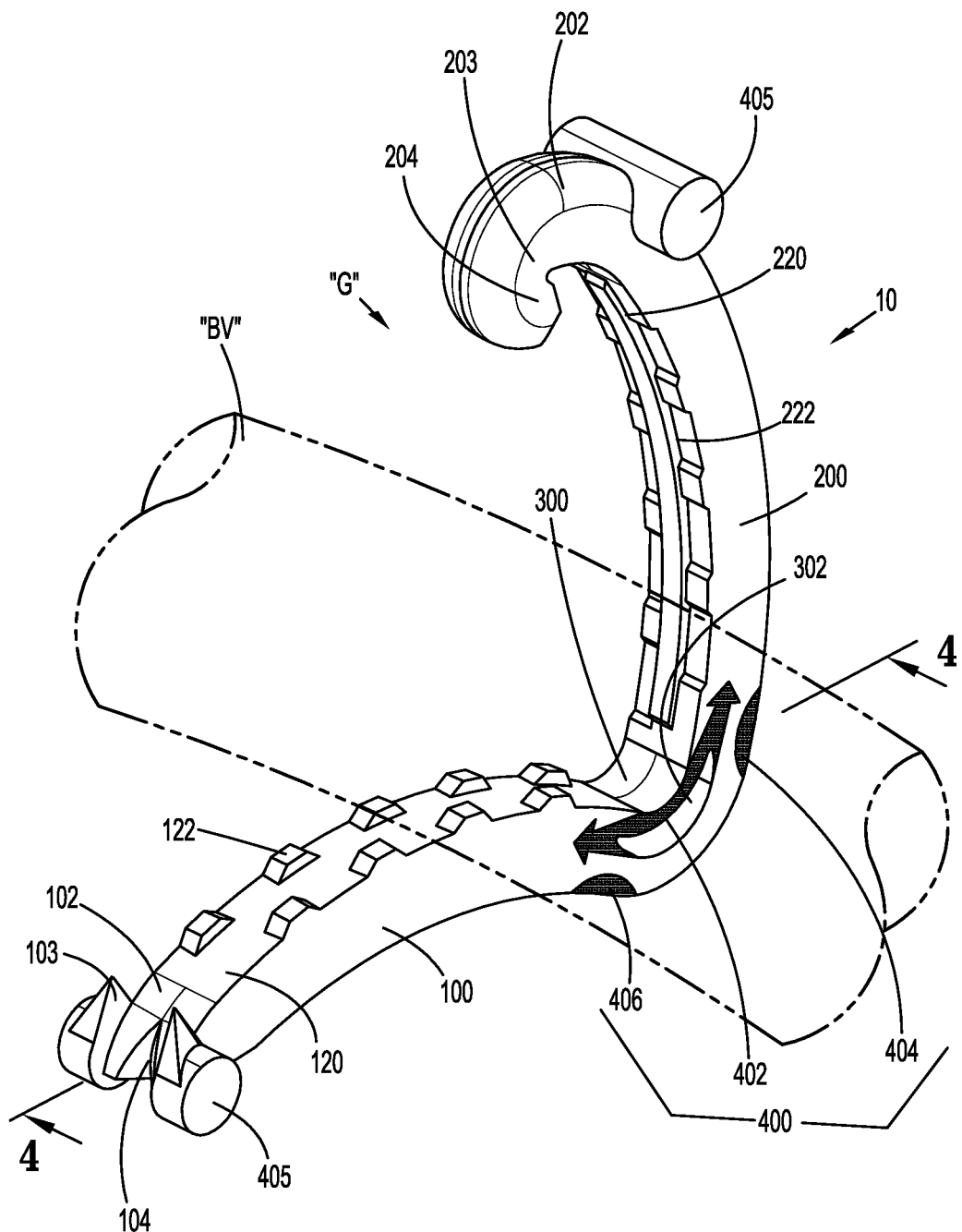
FIG. 1 is a perspective view of a ligation clip in accordance with the disclosure.

The disclosed ligation clip will now be described in detail with reference to the drawings in which like reference numerals designate identical or corresponding elements in each of the several views. However, it is to be understood that the disclosed aspects of the ligation clip are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as upper, lower, top, bottom, and similar terms are used to assist in understanding the description and are not intended to limit the disclosure.

In this description, the term "endoscopic" is used generally to refer to endoscopic, laparoscopic, arthroscopic, and/or any other procedure conducted through a small diameter incision or cannula. Further, the term "clinician" is used generally to refer to medical personnel including doctors, nurses, and support personnel. Finally, the term "substantially" is used generally to refer to 90 percent to 110 percent of a referenced parameter.

A surgical ligation clip in accordance with the disclosure is generally shown in FIGS. 1-5 as a ligation clip 10. The ligation clip 10 may be delivered to a surgical site for application to tissue, e.g., a body vessel. The ligation clip 10 includes the first and second arms 100, 200 and a hinge portion 300 interconnecting the first and second arms 100, 200. The first and second arms 100, 200 may be moved to a clamped configuration (FIG. 5) during application of the ligation clip 10 to body tissue. The ligation clip further includes a flexible insert assembly 400. In particular, the flexible insert assembly 400 is provided at, e.g., stress points along the hinge portion 300 (the stress points may be obtained through finite element analysis), as will be described below. The flexible insert assembly 400 reduces deformation of the ligation clip 10 during, e.g., clamping of tissue and storage of the ligation clip 10.

Figure 5:
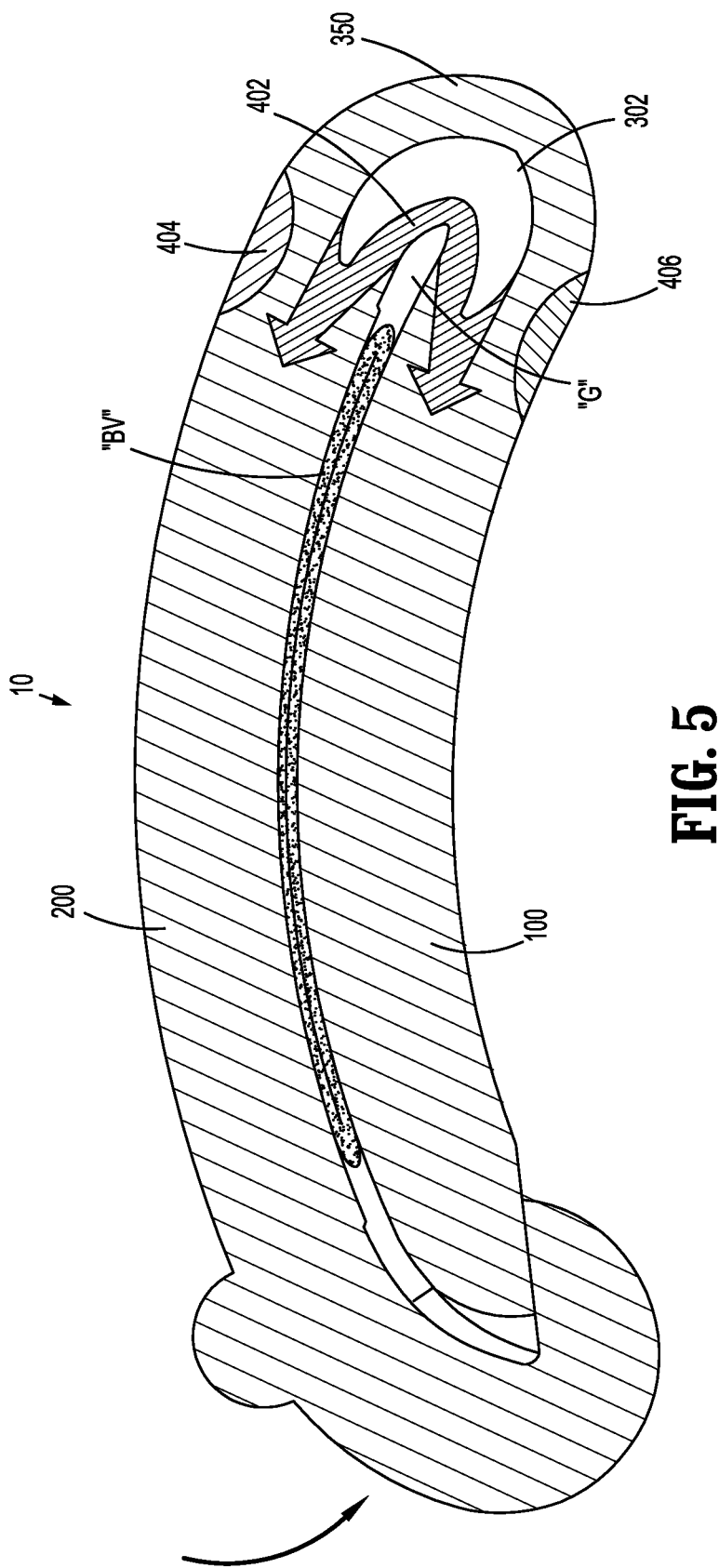
FIG. 5 is a cross-sectional view of the ligation clip of FIG. 4, illustrating a clamped configuration.

FIG. 1 illustrates the ligation clip 10 in an open configuration (FIG. 1), in which, the first and second arms 100, 200 are spaced from each other to define a gap "G" to receive tissue, e.g., body vessel "BV." The ligation clip 10 may be formed as a single unitary construct that has a V-shaped configuration. The first and second distal portions 102, 202 have latch portions 103, 203 that are movable into engagement with each other to retain the ligation clip 10 in the clamped configuration (FIG. 5). The first distal portion 102 defines a recess 104, and the second distal portion 202 has a hook portion 204 configured to be received in the recess 104 to secure the first and second arms 100, 200 together in order to clamp tissue between the first and second arms 100, 200.

In addition, the first arm 100 includes an inner clamping surface 120 having a plurality of teeth 122. The second arm 200 includes an inner clamping surface 220 defining a plurality of grooves 222 to receive the plurality of teeth 122 of the first arm 100. Under such a configuration, slippage of the target tissue may be reduced. In some aspects of the disclosure, the first and second distal portions 102, 202 may include posts 405 that have a substantially circular shape. The posts 405 may be received within recesses in jaws of a clip applier to retain the ligation clip 10 within the clip applier prior to application of the ligation clip 10 to tissue.

FIG. 1 further illustrates the hinge portion 300 interconnecting the first and second arms 100, 200. The hinge portion 300 defines a bore 302 having, e.g., a crescent or semi-circular shape, to improve flexing of the hinge portion 300 during clamping of tissue. In particular, the shape of the bore 302 may correspond to the curvature of the hinge portion 300. The bore 302 may also be centrally defined with respect to the hinge portion 300.

Figure 2:
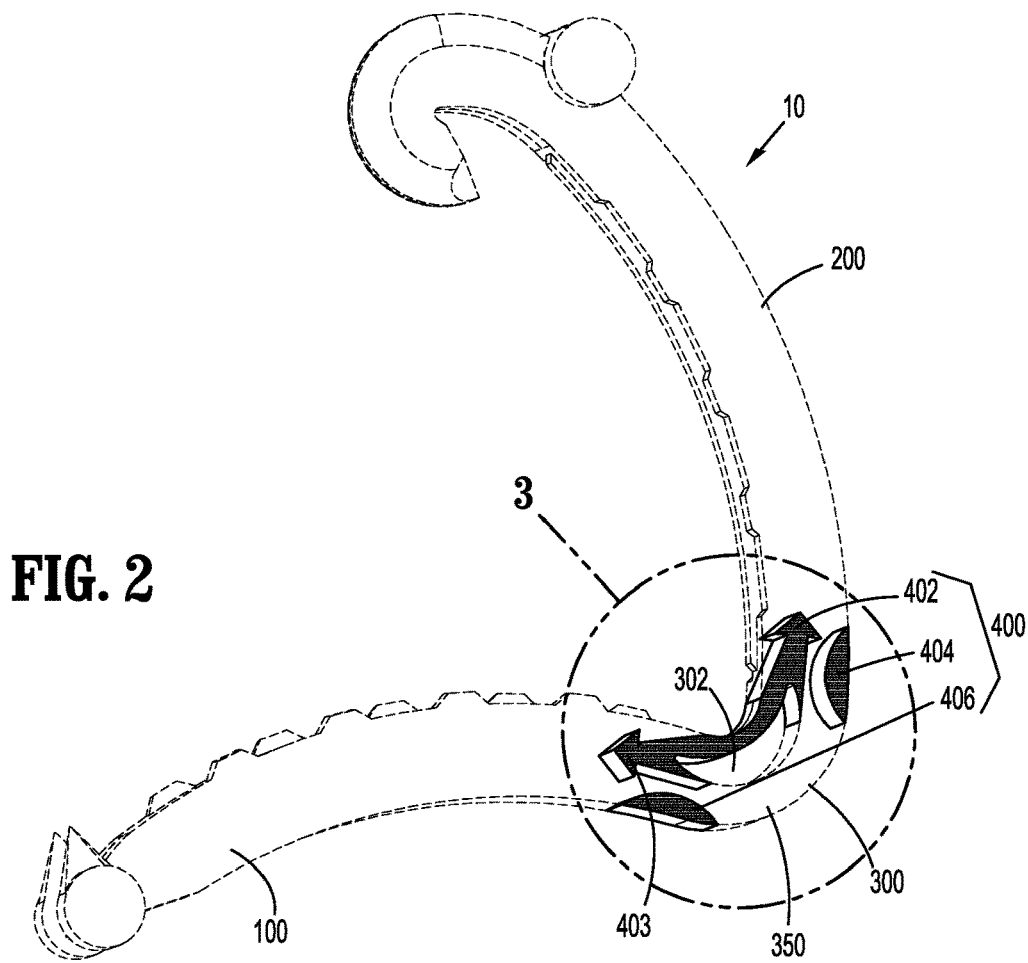
FIG. 2 is a perspective view of a flexible insert assembly of the ligation clip of FIG. 1 shown in phantom.
Figure 3:
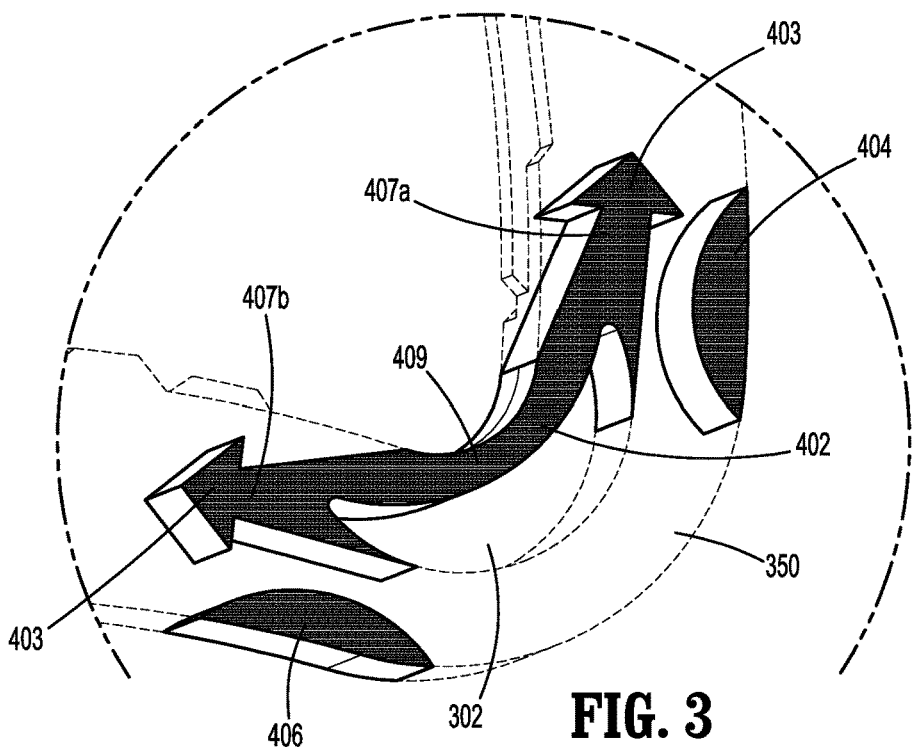
FIG. 3 is an enlarged view of the indicated area of detail of FIG. 2.
Figure 4:
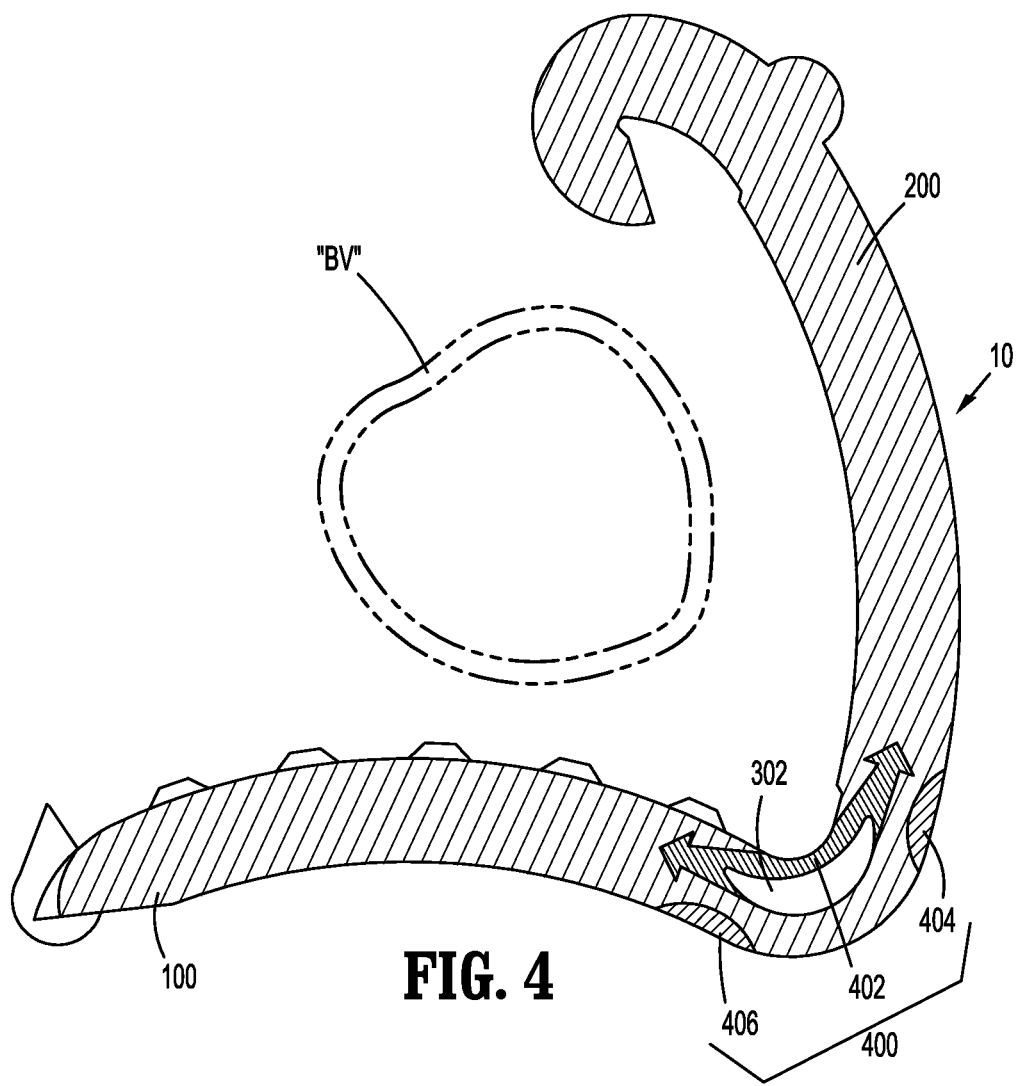
FIG. 4 is a cross-sectional view of the ligation clip of FIG. 1 taken along section line 4-4 of FIG. 1.

FIGS. 2 and 3 illustrate the hinge portion 300 including a body portion 350 and the flexible insert assembly 400. The flexible insert assembly 400 includes first, second, and third inserts 402, 404, 406 that are disposed on stress points on the body portion 350 that occur during clamping of the ligation clip 10. Such stress points along the body portion 350 may be obtained through finite element analysis. The first, second, and third inserts 402, 404, 406 may be embedded in the body portion 350 through, e.g., injection molding. In particular, the first insert 402 is in communication with the bore 302 and at least partially extends around a peripheral portion of the bore 302. The first insert 402 includes opposing wings 407a, 407b that laterally extend from the bore 302, and an inner wall 409 that defines part of the bore 302. The opposing wings 407a, 407b include respective anchoring portions 403 that inhibit relative movement between the first insert 402 and the body portion 350 of the hinge portion 300. The second and third inserts 404, 406 are spaced apart adjacent opposing sides of the bore 302 and define a portion of an outer surface of the ligation clip 10. The second and third inserts 404, 406 may be mirror images of each other. In particular, the second and third inserts 404, 406 may have, e.g., semi-circular shape. The first and second arms 100, 200 may be formed of a first material having a first rigidity or flexibility. The body 350 portion of the hinge portion 300 may be formed of a second material having a second rigidity or flexibility different from the first rigidity or flexibility. The flexible insert assembly 400 may be formed of a third material having a third rigidity or flexibility different from the first and/or second rigidity or flexibility. For example, the flexible insert assembly 400 may be formed of a material more flexible than the body portion 350 of the hinge assembly 300. The body portion 350 may be more flexible than the first and second arms 100, 200. In addition, the first insert 402 may be more flexible than the second and third inserts 404, 406 or vice versa. The second and third inserts 404, 406 may be formed of the same material having the same flexibility. However, it is contemplated that the second and third inserts 404, 406 may be formed of different materials having different flexibility. Under such a configuration, when the first and second arms 100, 200 transition to the clamped configuration, the flexible insert assembly 400 facilitates flexing of the hinge portion 300 and reduces or eliminates, e.g., plastic, deformation of the ligation clip 10, e.g., on the stress points occupied by the first, second, and third inserts 402, 404, 406.

The ligation clip 10 described above is formed of a resilient material that enables transition of the ligation clip 10 between the open configuration, in which, the first and second distal portions 102, 202 of the ligation clip 10 define a mouth or opening, and the clamped configuration, in which, the second distal portion 202 of the second arm 200 is releasably secured to the first distal portion 102 of the first arm 100 to clamp tissue between the first and second arms 100, 200. In the clamped configuration, the inner clamping surfaces 120, 220 of the first and second arms 100, 200, respectively, are in juxtaposed alignment.

In some aspects of the disclosure, the ligation clip 10 is formed of a polymeric material such as polyethylene terephthalate (PET), polybutylene terephthalate (PBT), polyoxymethylene, or other thermoplastic materials having similar properties that can be injection molded, extruded, or otherwise processed. It is also envisioned that portion of the ligation clip 10 may be formed from other materials including metals. Each of the first and second arms 100, 200 of the ligation clip 10 may be formed at least in part of a resilient bioabsorbable and/or biocompatible polymeric material. Examples of suitable bioabsorbable and/or biocompatible polymeric materials include acetal polyoxymethylene (POM), polyethylene terephthalate (PET), polybutylene terephthalate (PBT), polyoxymethylene, polyetheretherketone (PEEK), polypropylene, and polyethylene or other thermoplastic materials having similar properties that can be injection molded. The ligation clip 10 may also be made at least in part of a polymeric material or materials in combination with radiolucent metal alloys. Alternately, other materials may be used to form the ligation clip 10 including biocompatible metals, plastics and composites.

The ligation clip 10 may be utilized in, e.g., an anastomosis procedure. Anastomosis is an artificial connection of two vessel portions made by a surgeon and is required when a diseased portion of a vessel, e.g., artery, vein, or intestine, is removed from the vessel and the remaining vessel portions are rejoined. In use, it is envisioned that the first and second arms 100, 200 will be delivered to a surgical site by a clip applier (not shown) with the first and second arms 100, 200 of the ligation clip 10 supported in spaced relation to each other in the clip applier. It is also envisioned that the first and second arms 100, 200 will be aligned by and within the clip applier (not shown) prior to application to tissue. As stated above, one or both of the posts 405 may be received within grooves or slots in the clip applier to support and/or guide the ligation clips 10 within and along the clip applier.

Initially, the ligation clip 10 may be in the open configuration (FIG. 4) to receive a blood vessel "BV" between the first and second arms 100, 200. The latch portions 103, 203 of the first and second arms 100, 200 may engage each other, i.e., the hook portion 204 of the second arm 200 may be received in the recess 104 of the first arm 100. The body vessel "BV" (FIG. 5) is compressed between the inner clamping surfaces 120, 220 of the first and second arms 100, 200 to ligate the body vessel "BV." At this time, the first, second, and third inserts 402, 4004, 406 flex to facilitate clamping of the ligation clap 10 without causing, e.g., plastic, deformation in the ligation clip 10. In particular, when the first insert 402 is flexed, the wings 407a, 407b substantially oppose each other in a superposed relation, and the bore 302 conforms to the flexing of the hinge portion 300. Such a configuration facilitates flexing of the ligation clip 10 to enhance transition between the open and clamped configurations without causing, e.g., plastic, deformation of the ligation clip 10.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A ligation clip comprising:
   a first arm including a first clamping surface and a first latching structure;
   a second arm including a second clamping surface and a second latching structure; and
   a hinge portion interconnecting the first arm and the second arm, the hinge portion defining a bore and including a body portion and a flexible insert assembly having a first insert, a second insert, and a third insert, the first arm and the second arm being transitionable between an open configuration, in which the first arm and the second arm are spaced apart, and a clamped configuration, in which the first latching structure of the first arm and the second latching structure of the second arm engage each other to clamp tissue between the first clamping surface and the second clamping surface,
   wherein the first arm and the second arm have a first rigidity, wherein the body portion of the hinge portion has a second rigidity less than the first rigidity, and wherein at least one of the first insert, the second insert, or the third insert of the flexible insert assembly of the hinge portion has a third rigidity less than the second rigidity.

2. The ligation clip according to claim 1, wherein the bore of the hinge portion has a crescent shape when the first arm and the second arm are in the open configuration.

3. The ligation clip according to claim 1, wherein the second insert and the third insert of the flexible insert assembly are disposed adjacent respective ends of the bore of the hinge portion.

4. The ligation clip according to claim 1, wherein the first insert of the flexible insert assembly partially defines the bore of the hinge portion.

5. The ligation clip according to claim 1, wherein the first insert includes an anchor portion configured to inhibit movement of the first insert relative to the body portion of the hinge portion.

6. The ligation clip according to claim 5, wherein the anchor portion has a shape of an arrow.

7. The ligation clip according to claim 1, wherein the first latching structure or the second latching structure is a hook.

8. The ligation clip according to claim 1, wherein the first insert has the third rigidity, and wherein the third rigidity of the first insert is different from a fourth rigidity of at least one of the second insert or the third insert.

9. The ligation clip according to claim 8, wherein the second insert has the fourth rigidity, and wherein the fourth rigidity is different from a fifth rigidity of the third insert of the flexible insert assembly.

10. The ligation clip according to claim 1, wherein the first insert, the second insert, or the third insert is formed of a polymer.

11. The ligation clip according to claim 1, wherein the ligation clip is formed of an absorbable polymer.

12. The ligation clip according to claim 1, wherein at least one of the second insert or the third insert has a semi-circular shape.

13. The ligation clip according to claim 1, wherein at least one of the first clamping surface or the second clamping surface includes teeth to grip tissue.

14. A ligation clip comprising:
   a first arm including a first clamping surface and a second arm including a second clamping surface, the first arm being movable in relation to the second arm to move the ligation clip from an open configuration, in which the first clamping surface and the second clamping surface are spaced apart, to a clamped configuration, in which at least portions of the first arm and the second arm engage each other to clamp tissue between the first clamping surface and the second clamping surface; and a hinge portion interconnecting the first arm and the second arm, the hinge portion including a body portion and flexible inserts embedded in the body portion, the flexible inserts having a first rigidity less than a second rigidity of the body portion, the flexible inserts peripherally arranged about the hinge portion and spaced apart from each other.

15. The ligation clip according to claim 14, wherein the first arm and the second arm include respective latch portions engaging each other when the ligation clip is in the clamped configuration to retain the first arm and the second arm in the clamped configuration.

16. The ligation clip according to claim 14, wherein the flexible inserts include a pair of semi-circular inserts.

17. The ligation clip according to claim 14, wherein the hinge portion defines a bore.

18. The ligation clip according to claim 17, wherein the bore of the hinge portion has a crescent shape when the ligation clip is in the open configuration.

19. The ligation clip according to claim 17, wherein the flexible inserts include a central insert disposed adjacent the bore.

20. The ligation clip according to claim 19, wherein the central insert includes an anchor portion configured to inhibit movement of the central insert relative to the body portion of the hinge portion.

\* \* \* \* \*